United States Patent [19]

Soderstrom

[11] 4,252,651
[45] Feb. 24, 1981

[54] NEGATIVE PRESSURE VALVING SYSTEM AND TRANSMEMBRANE PRESSURE ALARM SYSTEM

[75] Inventor: Jan Soderstrom, Cary, Ill.

[73] Assignee: Baxter Travenol Laboratories, Inc., Deerfield, Ill.

[21] Appl. No.: 70,871

[22] Filed: Aug. 29, 1979

Related U.S. Application Data

[63] Continuation of Ser. No. 841,357, Oct. 12, 1977, abandoned.

[51] Int. Cl.³ .......................... B01D 33/40; F15B 5/00
[52] U.S. Cl. ...................................... 210/97; 210/130; 210/143; 210/321.3; 128/214 R; 137/82; 137/625.64; 204/306
[58] Field of Search ...................... 210/22, 23, 90, 97, 210/130, 143, 321, 416 R, 433 M; 128/214 R; 204/252, 306; 137/82, 625.64

[56] References Cited

U.S. PATENT DOCUMENTS

| | | | |
|---|---|---|---|
| 2,915,077 | 12/1959 | Wehrli et al. | 137/82 |
| 2,931,343 | 4/1960 | Moog, Jr. | 137/82 X |
| 3,515,275 | 6/1970 | Bowman | 210/22 |
| 3,795,318 | 3/1974 | Crane et al. | 210/321 B |
| 3,878,095 | 4/1925 | Frasier et al. | 210/321 B |
| 3,946,731 | 3/1976 | Lichtenstein | 210/23 F X |
| 4,098,274 | 7/1978 | Ebling et al. | 210/321 B X |

Primary Examiner—Ferris H. Lander
Attorney, Agent, or Firm—Paul C. Flattery; Gerald S. Geren

[57] ABSTRACT

There is disclosed herein a negative pressure dialysis machine which includes a negative pressure valving system and transmembrane pressure alarm system.

An electromagnetically controlled flapper valve is disclosed herein for use as a negative pressure control valve. The flapper valve permits accurate control of negative pressure and changes in negative pressure to be affected rapidly.

Transmembrane pressure alarm systems are provided which detect the difference in pressure between the blood and dialysate in the dialyzer and activate alarms and prevent dialysis (a) if the dialysate pressure exceeds the blood pressure and/or (b) if a blood pressure signal is not received which would permit actual transmembrane pressure to increase beyond a predetermined limit.

7 Claims, 4 Drawing Figures

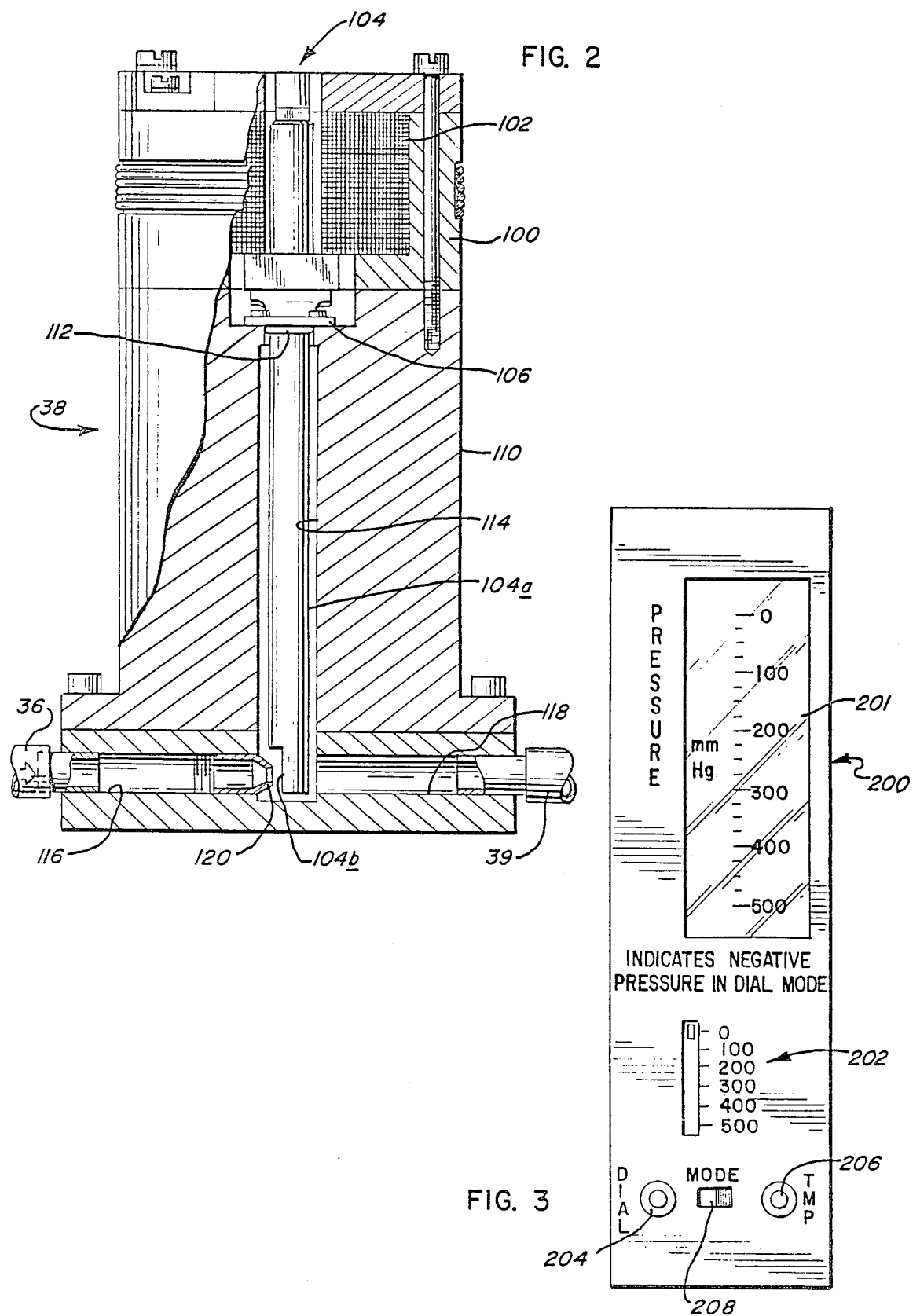

NEGATIVE PRESSURE VALVING SYSTEM AND TRANSMEMBRANE PRESSURE ALARM SYSTEM

This is a continuation of application Ser. No. 841,357, filed Oct. 12, 1977 and now abandoned.

BACKGROUND OF THE INVENTION

The invention relates to dialysis machines, and more particularly, to a negative pressure valve system and to alarm systems for use in such machines.

In dialysis, a patient's blood and dialysate flow through a dialyzer which includes a semipermeable membrane for separating the blood and the dialysate. Impurities and water from the blood cross the membrane and enter the dialysate for disposal. The terms dialysate, dialysis solution and dialyzing fluid as may be used hereinafter are intended to be synonomous.

In some dialyzers the dialysate is drawn through the dialyzer under a negative pressure (i.e., below atmospheric pressure). Such systems normally include a negative pressure pump positioned downstream of the dialyzer for drawing the dialysate through the dialyzer and a negative pressure valve positioned upstream of the dialyzer. The negative pressure in the dialyzer is controlled by adjustment of the negative pressure control valve. Although these systems are commonly referred to as negative pressure systems, there are certain conditions under which positive dialysate pressures may be generated. U.S. Pat. No. 3,878,095 discloses one such negative pressure system.

In some machines electromechanically operated needle valves have been used as the negative pressure control valve. Such valves have an operating characteristic such that as the valve moves from the open position toward the closed position, the change in pressure is relatively small and linear. However as the valve is about to close, the pressure becomes increasingly negative at a very rapid rate until the valve closes. In other words, as the valve closes, there are very great changes in pressure. This steep change in pressure makes it difficult to accurately control and maintain the negative pressure at highly negative levels (e.g., $-400$ to $-500$ mm Hg). This is particularly true in an electromechanical system wherein gear tolerances and changes in temperature also affect the control and positioning of the needle valve and thus the negative pressure.

Furthermore, the electromechanical system includes a constant speed DC motor to operate the valve. Therefore, since the valve characteristics are relatively linear, the time necessary to induce large changes in negative pressure may be relatively long. For example, the change from $-200$ mm Hg to 0 mm Hg may take on the order of two minutes.

It is therefore an object of this invention to provide a more accurately controllable and more responsive negative pressure valve system.

In dialysis the pressure differential across the semipermeable membrane (i.e., the difference in pressure between the blood and the dialysate) is important. This differential may be referred to as the transmembrane pressure. However, in the event that the dialysate pressure exceeds the blood pressure, impurities in the dialysate could undesirably pass through the membrane and into the blood.

It is desirable, therefore, that dialysis be prevented in the event that the dialysate pressure exceeds the blood pressure.

During dialysis, water is removed from the blood by a process known as ultrafiltration. The quantity of water removed is directly related to the transmembrane pressure. It is desirable to control the amount of water removed since removal of too much water during dialysis may result in undesirable side effects.

Therefore, it is desirable to maintain control over the difference between the dialysate pressure and blood pressure so as to control ultrafiltration.

Some prior art dialysis machines have included transmembrane pressure monitors, which merely measured and displayed the transmembrane pressure. In another machine, provisions were made for alarms in the event the transmembrane pressure exceeded a predetermined value. The alarms included a tolerance or alarm window of, for example, 50 mm Hg above or below the predetermined value. Therefore, in the event that the transmembrane pressure was zero, it is possible that with those tolerances dialysate pressure could increase beyond the blood pressure level, thereby permitting undesirable transfer from the dialysate to the blood.

It is therefore an object of this invention to provide an alarm system for preventing dialysis if the dialysate pressure exceeds the blood pressure.

In order to maintain a set or predetermined transmembrane pressure, both the dialysate pressure and the blood pressure must be monitored. In the event that the blood pressure signal is not received by the transmembrane pressure control system, it is possible that the actual transmembrane pressure could undesirably exceed the set or predetermined pressure without providing any indication or alarm as to that actual increase.

It is therefore another object of this invention to provide a system whereby the actual transmembrane pressure is maintained at a set or predetermined level, and in the event of signal failure from the venous pressure transducer, appropriate alarms and shut-off mechanisms are activated.

These and other objects of the invention will become apparent in the following description and appended claims.

SUMMARY OF THE INVENTION

There is provided by this invention a negative pressure control system which provides for very accurate and very responsive control of negative pressure. An electromagnetically controlled flapper valve is provided for controlling the negative pressure. It has been found that this valve permits very rapid response times in terms of the stabilization of the negative pressure in the system. This rapid response time (on the order of 30 seconds) has been found to be very desirable from physiological, safety and/or convenience points of view.

This invention also includes transmembrane pressure alarm systems which prevent the dialysate pressure from exceeding the blood pressure. Another feature of transmembrane alarm system is that the transmembrane pressure will be maintained at a set or predetermined level during operation of the machine, and in the event that no venous pressure signal is received or the venous pressure becomes negative below a predetermined level, the system will alarm and prevent further dialysis.

BRIEF DESCRIPTION OF THE DRAWINGS

FIG. 2 is a broken away and sectional view showing the details of the negative pressure control flapper valve;

FIG. 3 is a front view of a transmembrane/dialysate pressure module; and

DESCRIPTION OF THE PREFERRED EMBODIMENT

I. In General

Figure 1:
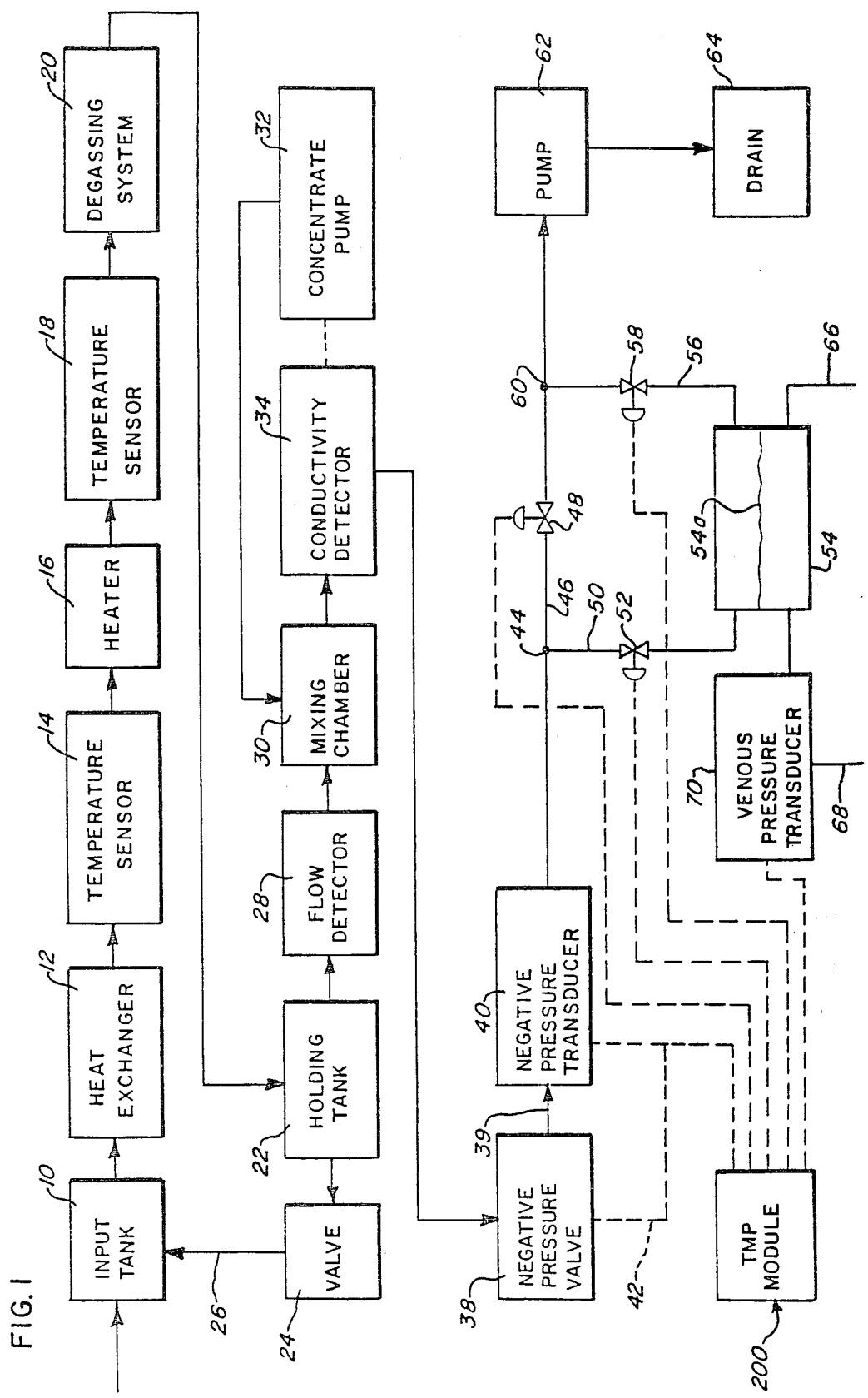
FIG. 1 is a flow diagram depicting the fluid flow path within the dialysis machine.

Referring now to FIG. 1, the dialysis machine is shown in block diagram form.

Incoming water flows to the holding tank 10. From the holding tank the water flows through a heat exchanger 12, a first temperature sensor 14, through an electric heater 16, and to a second temperature sensor 18. The heated water then flows from the second temperature sensor 18 to a degassing section 20, which includes a restriction and degassing pump. Degassed water then flows to a holding tank 22, which is connected at its upper end to a pressure relief valve 24 and through a return line 26 to the input tank 10. Degassed water flows from the holding tank 22 through a flow detector 28 and to a dialysate mixing chamber 30. Dialysate concentrate flows to the mixing chamber 30 from a concentrate pump 32 and mixes with the degassed water. The amount of concentrate delivered to the mixing chamber by the pump 32 is controlled by a conductivity detector 34 that is positioned immediately downstream of the mixing chamber 30.

The dialysate which has been prepared then flows via line 36 to the negative pressure or dialysate pressure control valve 38, through line 39 and to a negative pressure or dialysate pressure transducer 40. The transducer 40 and negative pressure valve 38 are connected through a feedback loop 42 for controlling the valve 38 and the negative pressure.

The dialysate then flows from the transducer 40 to a junction 44, at which point the flow lines divide into two branches. One branch is a dialyzer bypass line 46 which includes a bypass control valve 48. The other branch includes a dialyzer inlet line 50, having an inlet control valve 52 positioned therein. A negative-pressure-type dialyzer 54 is positioned downstream of the valve 52, and the downstream end of the dialyzer connects to the outlet line 56, outlet control valve 58 and to the junction 60.

A negative pressure pump 62 is positioned downstream of the junction 60 for drawing dialysate through the system and particularly through the negative pressure valve 38 and the dialyzer 54. Used or spent dialysate flows from negative pressure pump 62 to the drain 64.

The dialyzer 54 includes a semipermeable membrane, shown illustratively as 54a, which separates the dialysate from the blood side of the dialyzer. A patient's blood enters the dialyzer via the arterial line 66 and exits the dialyzer via the venous line 68. A pressure transducer 70 is positioned in the venous line 68 to detect the blood pressure at that point.

The mean transmembrane pressure within the dialyzer is approximated by measuring the difference between the pressure measured by the venous pressure transducer 70 and that measured by the negative pressure transducer 40. Both the venous pressure transducer 70 and the negative pressure transducer 40 are connected to the transmembrane/dialysate pressure module 200.

II. The Negative Pressure Control System

Referring now to FIG. 2, there is shown an electromagnetically operated flapper-type negative pressure valve assembly 38, to which the input line 36 and the output line 39 are connected. Electromagnetically-operated flapper valves are sold by Hydraulic Servo System Corp., 5800 Transit Road, Depew, N.Y. 14042. (Model 58 valve when modified, has been found to be generally suitable for a negative pressure control valve in a dialysis machine.)

The valve assembly 38 includes a magnet frame 100 within which is positioned a magnet coil 102. An elongated rod or armature 104 is provided and its upper section is positioned in the coil. The armature is connected to a flat leaf spring-like member 106 which permits the armature to pivot and which is adjusted to bias the armature to a first position.

A flow housing 110 is secured to the bottom of the magnetic frame, the spring-like member 106 is secured to the housing, and the O-ring 112 seals the armature 104 to the housing. The housing 110 includes: a central bore 114; an inlet bore 116 and an outlet bore 118, which are axially aligned; and a flow orifice or nozzle 120 which is positioned at the outlet end of the inlet bore 116. The inlet bore is connected to the line 36 and the outlet bore 118 is connected to the line 39.

The armature 104 includes an elongated lower section 104a which is positioned within the central bore 114. The lower end of the armature includes flat land portion 104b which faces the orifice 120 and is constructed to seat thereagainst. The positioning of the land 104b relative to the nozzle 120 establishes the pressure drop or negative pressure across the negative pressure valve. The level of negative pressure is related to the distance between the land 104b and the orifice 120. In other words, the closer the land is to the orifice, the more negative the pressure, and the further the land is from the orifice, the less negative the pressure. In this application the lower section 104a has a length greater than the length of the upper section so as to permit control of the positioning of the land and operation of the system under dialysate positive pressure. The length of the lower section in this valve is several times greater than the length of the lower section in the standard model 58, and under the same system constraints positive dialysate pressures could not be obtained with the standard model 58. It has been found that the valve disclosed herein has an operating characteristic which is substantially linear.

The position of the armature relative to the orifice is controlled by controlling the current flow through the magnetic coil. The armature is biased by the spring-like member 106 to a first position, such that when there is no current flow, the valve is in an open position, away from the orifice, and there is a very small pressure drop across the valve.

The magnetic coil 102 is operatively associated with the transducer 40 through a buffered operational amplifier. It will be appreciated that the long length of the lower section (i.e., the distance between the pivot 106 and the land 104) permits of very carefully controlled incremental changes in the distance between the orifice and the land. Therefore, positioning of the land 104b relative to the orifice 120 can be controlled by very small changes in the current flow to the magnetic coil 102. This is true throughout substantially the entire operating range of the valve.

As the current flow through the coil increases, the upper section of the armature is pulled against biasing spring, and the land section 104b is moved toward the orifice 120, which increases the negative pressure. It has been found that negative pressure increases substantially linearly with increasing current flow through the coil. Thus the positioning of the land and the negative pressure can be controlled very accurately, even at highly negative values, such as −400 or −500 mm Hg.

Furthermore, since the only moving part in the system is the armature and the operating characteristics are substantially linear, the response time to change the negative pressure at the valve is very small. The time required for the entire system to adjust to changes in the negative pressure and stabilize are related to system constraints. In this system, the response time to change from −200 mm Hg to 0 mm Hg is on the order of 30 seconds. Different systems may respond in longer or shorter times depending upon system constraints.

Flapper valve assemblies, such as 38, are believed to be readily interchangeable between dialysis machines so as to avoid problems in calibration and standardizing equipment when replacing the valve assemblies.

III. Transmembrane Pressure Controls

The dialysis machine as used herein can be referred to as a proportional dialysate delivery system as sold by Baxter Travenol Laboratories, Inc., under the name *Proportioning Dialyzing Fluid Delivery System* (5M 1352–5M 1355). These machines are in modular form whereby various functions can occur within the movable and serviceable modules. FIG. 3 shows the front panel of a transmembrane/dialysate pressure module 200. The panel shows a negative pressure gauge 201 which provides for negative pressure readings of zero (0) to −500 mm Hg. A slide control 202 is provided for setting transmembrane pressure, as will be described hereinafter.

This module can be operated either in a dialysate pressure mode or a transmembrane pressure mode. Indicator light 204 will be lit when the machine is in the dialysate pressure mode, and light 206 will be lit when the machine is operated in the transmembrane pressure mode. Switch 208 permits selection of operation in either the transmembrane pressure or dialysate pressure mode. During set-up and initial operation of the machine, the module is operated in the dialysate pressure mode. Once stabilized, the module may be switched to the transmembrane pressure mode.

The transmembrane pressure in the dialyzer is approximated by measuring the difference between the pressure indicated by the venous pressure transducer 70 and the negative pressure transducer 40. For example, if the venous pressure is +50 and the negative pressure is −200, the transmembrane pressure is 250.

The operator can select a desired transmembrane pressure by use of the slide control 202. For example, the transmembrane pressure can be set at 300 and this pressure will be maintained automatically through the operation of the negative pressure control valve 38 as the venous pressure varies. Use of the flapper valve 38 thus is very advantageous in that the negative pressure changes can quickly follow or "track" changes in the venous blood pressure.

III. A. Zero Transmembrane Pressure Alarm Condition

There are circumstances in which the operator desires that the transmembrane pressure be zero (i.e., no pressure differential across the membrane). However, the dialysate pressure should never exceed the blood pressure since undesirable impurities may then pass through the semipermeable membrane and into the blood.

Under normal operating circumstances, an "alarm window" of +50 mm Hg is provided. For example, at 200 mm Hg, alarms would be activated if the transmembrane pressure is not within the pressure of 150–250 mm Hg. However, with any such alarm window, at a transmembrane pressure of 0 mm Hg, it is possible that the pressure on the dialysate side of the membrane could undesirably exceed the venous blood pressure.

As described hereinafter, means are provided for preventing dialysate pressure from exceeding the blood pressure and appropriate alarms are activated. In the event that the dialysate pressure exceeds the venous pressure, further dialysis is prevented by opening bypass valve 48 and closing the dialysis inlet and outlet valves 52 and 58. This effectively isolates the dialyzer and prevents the undesirable situation in which the dialysate pressure can increase above the blood pressure. Furthermore, audible and visible alarms are also activated.

Figure 4:
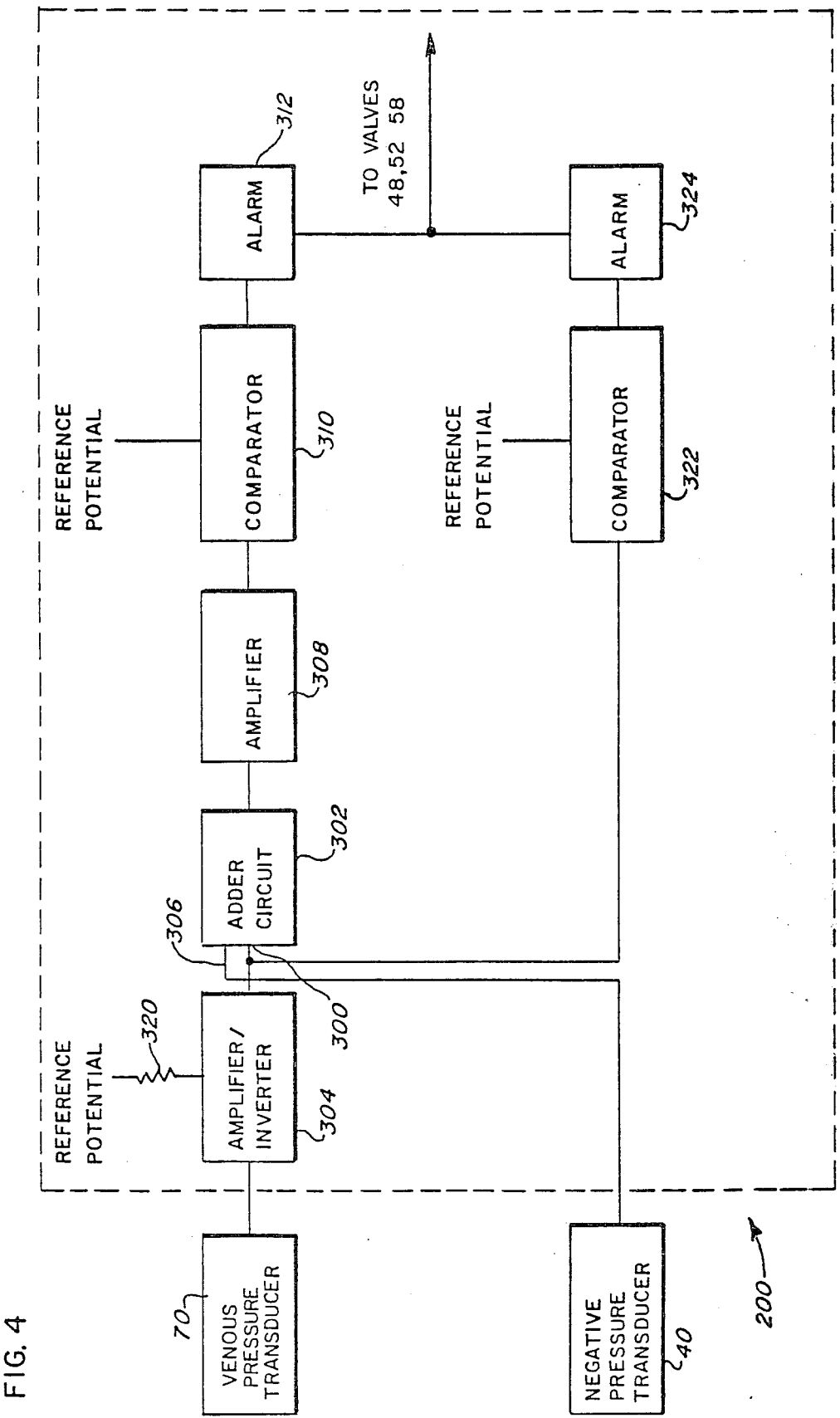
FIG. 4 is a block-type diagram showing the transmembrane alarm systems.

Referring now to FIG. 4, the dialysate flows through negative pressure transducer 40. Negative pressure transducer 40 includes an operational amplifier that develops a voltage which varies in accordance with the pressure on the transducer. When the pressure on the transducer 40 is negative in nature, a positive voltage is developed at the output of transducer 40; when the pressure on transducer 40 is positive, negative voltage is developed at the output of transducer 40. In the preferred embodiment, the signal developed at the output of negative pressure transducer 40 will be +1.6 volts at −100 mm Hg. At 0 mm Hg, the output of pressure transducer 40 will be 0 volts, and at +100 mm Hg, the output will be −1.6 volts. This voltage is coupled from transducer 40 to one input 300 of an adder circuit 302 in pressure module 200.

Venous pressure transducer 70 includes an operational amplifier circuit that develops a voltage which varies in accordance with the venous pressure at the transducer. In the preferred embodiment, the output of pressure transducer 70 will vary over a range of −2 volts at 0 mm Hg to −8 volts at 300 mm Hg. This output signal is coupled from pressure transducer 70 to an amplifier/inverter 304 in pressure module 200. Amplifier/inverter 304 provides a scaling factor adjustment to its output signal in addition to an inversion. Consequently, at the output of amplifier/inverter 304, the voltage will vary from 0 volts at 0 mm Hg to +4.8 volts at 300 mm Hg. The signal developed by amplifier/inverter 304 is coupled to a second input 306 of adder circuit 302.

Adder circuit 302 adds the signals coupled to inputs 300 and 306 and develops an output signal corresponding to the sum of the signals at inputs 300 and 306. For example, if the dialysate pressure is −100 mm Hg, the voltage coupled to input 300 will be +1.6 volts. If the venous pressure is also 100 mm Hg, +1.6 volts will be coupled to input 306. The output of adder circuit 302 would then be 3.2 volts. The output of adder circuit 302 is coupled to an amplifier 308 where it is amplified and coupled to a comparator 310.

Comparator 310 compares the signal coupled from the amplifier 308 to a reference voltage. If the signal from amplifier 308 exceeds the reference voltage, comparator 310 will develop an output signal which is coupled to the alarm circuit 312 actuating audible and visible alarms. Alarm circuit 312 is also coupled to valves 48, 52 and 58 in order to open valve 48 and close valves 52 and 58.

In the preferred embodiment, should the dialysate pressure become positive rather than negative, the voltage developed at the output of transducer 40 will become positive. If, for example, the dialysate pressure becomes +100 mm Hg, the voltage at input 300 will be −1.6 volts. The blood pressure as sensed by transducer 70 remains at 100 mm Hg so that the dialysate pressure and blood pressure are identical. In this circumstance, the output of amplifier/inverter 304 will develop a voltage of +1.6 volts which is coupled to input 306 of adder circuit 302. Adder circuit 302 will add the voltages developed at the two inputs and will develop an output voltage of 0 volts. The 0 volt signal developed by adder circuit 302 is coupled to amplifier 308 and from amplifier 308 to comparator 310. A 0 volt signal, indicating identity of pressure between pressure transducer 70 and pressure transducer 40, and any more positive signal, indicating a greater pressure at transducer 40 than at transducer 70, will actuate comparator 310 to develop an output signal and actuate the alarms in alarm circuit 312. Alarm circuit 312 will open valve 48 and close valves 52 and 58, thus bypassing the dialyzer 54.

III. B. Alarm Conditions for Loss of Venous Blood Pressure Signal

This alarm condition is intended to prevent the transmembrane pressure from increasing beyond a set limit. The venous pressure transducer 70 provides information to the pressure module for comparison with the signal from the negative pressure transducer 40 so as to maintain the appropriate transmembrane pressure.

It is possible that signals from the venous pressure transducer may not be received in the transmembrane pressure module, for example if there are faulty connections between the various modules of the machine. In this particular machine, if no signal is received, the machines assumes a venous pressure of −100 mm Hg. When operating properly and if the venous pressure signal is +200 and the desired transmembrane pressure is set at 300, then the dialysate pressure would be controlled to −100. However, if no signal is received, the machine would assume a venous pressure of −100 (even though the actual pressure was +200). Based on the −100 indication, the transmembrane pressure module operates the negative pressure controls to permit the negative pressure to reach −400. Therefore, the actual transmembrane pressure would be 600 (i.e., the actual venous pressure of +200 less the actual dialysate pressure of −400). However, the displayed transmembrane pressure would be only 300 and no alarm would have been activated.

As described hereinafter, there is provided electronic circuitry for (1) preventing further dialysis by bypassing and isolating the dialyzer through the valves 48, 52 and 58, and (2) activating audible and visual alarms when no signal from the venous pressure transducer is applied to the pressure module.

As previously noted, venous pressure transducer 70 includes an operational amplifier circuit that develops a voltage which varies in accordance with the venous pressure at the transducer. Further, at the output of amplifier/inverter 304, the voltage will vary from 0 volts for 0 mm Hg to +4.8 volts for 300 mm Hg.

Resistor 320 is shown in FIG. 4 as being coupled between a reference potential and amplifier/inverter 304. Resistor 320 in the preferred embodiment is coupled to a positive voltage potential and has a value of approximately 200 K ohms. This resistor is generally termed in the art as a "pull-down" resistor.

The output of amplifier/inverter 304, in addition to going to adder circuit 302, also is coupled to the input of a comparator circuit 322. A reference voltage also is coupled to comparator 322. If the signal coupled to comparator 322 exceeds the reference voltage, comparator 322 will develop a comparison signal that is coupled to an alarm circuit 324. The comparison signal will actuate the audible and visual alarms contained in alarm circuit 324. Alarm circuit 324 also will open valve 48 and will close valves 52 and 58, thus bypassing membrane 54.

Should venous pressure transducer 70 be inadvertently disconnected from amplifier/inverter 304, or should the coupling therebetween be inadvertently broken, the input voltage coupled to amplifier/inverter 304 will be 0 volts. With an open connection at the input of amplifier/inverter 304, pull-down resistor 320 will cause the input to become positive. In the preferred embodiment, this will become positive with the voltage of approximately +0.5 volts, corresponding to a blood pressure more negative than −100 mm Hg. The output of amplifier/inverter 304 will now become negative rather than its normal positive condition. The +0.5 volts coupled to the input of amplifier/inverter 304 will cause the amplifier to develop −1.8 volts approximately at its output. This −1.8 volt signal is coupled to comparator 322 causing comparator 322 to develop a comparison signal that is coupled to alarm circuit 324. In the event that there is no open connection and the venous signal is less than 0 volts (i.e., −100 mm Hg), the alarms will still be actuated. As previously noted, alarm circuit 324 will actuate its audible and visual alarms, open valve 48 and close valves 52 and 58, thus preventing excessive transmembrane pressure.

It will be appreciated that numerous changes and modifications can be made in the embodiment disclosed herein without departing from the spirit and scope of this invention.

What is claimed is:

1. A dialysis machine for use with a negative pressure dialyzer which includes a negative pressure control valve positioned upstream of a dialyzer, a negative pressure sensing means operatively associated with said valve means positioned downstream thereof, and a negative pressure pump for drawing dialysate through said valve means and said dialyzer, wherein the improvement comprises said negative pressure valve means, comprising electromagnetically controllable flapper valve means for accurately controlling negative pressure to pressures as negative as about −400 mm/Hg, said valve means having substantially linear operating characteristics to pressures as negative as about −400 mm/Hg and said valve means also being effective to minimize the time in which said machine responds to changes in negative pressures.

2. A dialysis machine as in claim 1, wherein said flapper valve means includes,
   a body having electromagnet means at one end, flow housing means at the other end, and a central bore therethrough,
   elongated armature means having an upper and a lower section pivotally secured to said housing so that said upper section is surrounded by said magnet and said lower section extends into said flow housing, and
   said flow housing including dialysate inlet and outlet bores which are substantially axially aligned, said bores having inner ends which are spaced from each other, and said armature including land means in said lower section at the lower end thereof, said land means being positioned between the inner ends of said bores and movable toward and away from the inner end of said inlet bore, so as to controllably vary the negative pressure, in linear relation to the current flow through said magnet.

3. A dialysis apparatus as in claim 2, wherein said lower section of said armature means is substantially longer than the upper section thereof.

4. A dialysis apparatus as in claim 2, wherein there is further provided spring biasing means cooperatively associated with said armature for maintaining said armature in a first open position when there is no current flow through the magnet.

5. A dialysis apparatus as in claim 4, wherein there is further provided nozzle means at the inner end of said inlet bore, said nozzle arranged for cooperation with said land portion on said armature.

6. A dialysis machine as in claim 1, wherein flapper valve means includes a body having electromagnet means at one end, flow housing means at the other end, and a central bore therethrough, elongated armature means having an upper and a lower section pivotally secured to said housing so that said upper section is surrounded by said magnet and said lower section extends into said flow housing, with said lower section being of a length substantially greater than the length of said upper section so as to permit for accurate control of the positioning of said lower section.

7. A dialysis machine for use with a negative pressure dialyzer, said machine having a negative pressure control system for controlling the negative pressure at the dialyzer,
   said system including: a negative pressure control valve cooperatively associated with the dialyzer; negative pressure sensing means operatively associated with the dialyzer and said valve means; and negative pressure pump means for drawing dialysis solution through said valve means and said dialyzer; and
   wherein said negative pressure valve means comprises electromagnetically controllable flapper valve means for accurately controlling negative pressure to pressures as negative as about $-400$ mm/Hg, said valve means having substantially linear operating characteristics to pressures as negative as about $-400$ mm/Hg and said valve means also being effective to minimize the time in which said machine responds to changes in negative pressures.

* * * * *